US012601001B2

(12) United States Patent
Bossert-Reuther et al.

(10) Patent No.: US 12,601,001 B2
(45) Date of Patent: Apr. 14, 2026

(54) STABILIZATION OF NADPH OR NADH IN AMMONIA DETECTION ASSAYS

(71) Applicant: Roche Diagnostics Operations, Inc., Indianapolis, IN (US)

(72) Inventors: Steffen Bossert-Reuther, Mannheim (DE); Rolf Nagel, Mannheim (DE); Silvia Rettig, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1137 days.

(21) Appl. No.: 17/427,295

(22) PCT Filed: Jan. 30, 2020

(86) PCT No.: PCT/EP2020/052251
§ 371 (c)(1),
(2) Date: Jul. 30, 2021

(87) PCT Pub. No.: WO2020/157178
PCT Pub. Date: Aug. 6, 2020

(65) Prior Publication Data

US 2022/0112537 A1 Apr. 14, 2022

(30) Foreign Application Priority Data

Jan. 31, 2019 (EP) .................................... 19154870

(51) Int. Cl.
*C12Q 1/00* (2006.01)
*C12Q 1/32* (2006.01)
*C12Q 1/58* (2006.01)

(52) U.S. Cl.
CPC ............... *C12Q 1/008* (2013.01); *C12Q 1/32* (2013.01); *C12Q 1/58* (2013.01)

(58) Field of Classification Search
CPC . C12Q 1/008; C12Q 1/32; C12Q 1/58; G01N 33/84
See application file for complete search history.

(56) References Cited

U.S. PATENT DOCUMENTS

| | | | | |
|---|---|---|---|---|
| 3,929,581 | A * | 12/1975 | Da Fonseca-Wollheim | C12Q 1/58 435/26 |
| 4,394,449 | A | 7/1983 | Modrovich | |
| 4,704,365 | A | 11/1987 | Yost | |
| 5,037,738 | A | 8/1991 | Lamos et al. | |
| 5,141,853 | A * | 8/1992 | Kasal | G01N 33/84 435/26 |
| 5,589,348 | A * | 12/1996 | Kaufman | C12Q 1/32 435/26 |
| 5,773,585 | A | 6/1998 | Hongo et al. | |
| 5,888,528 | A | 3/1999 | Wellinghoff et al. | |
| 5,888,828 | A | 3/1999 | Tanaka et al. | |
| 6,107,052 | A | 8/2000 | Dorn | |
| 2007/0065896 | A1 | 3/2007 | Coombs et al. | |

FOREIGN PATENT DOCUMENTS

| | | | | |
|---|---|---|---|---|
| AU | 2004241364 | A1 | 12/2004 | |
| CN | 1920532 | A | 2/2007 | |
| CN | 101096701 | A | 1/2008 | |
| CN | 102297938 | A | 12/2011 | |
| CN | 102297960 | A | 12/2011 | |
| CN | 102298057 | A | 12/2011 | |
| CN | 107607524 | A | 1/2018 | |
| EP | 0135092 | A2 | 3/1985 | |
| JP | H02255099 | A | 10/1990 | |
| JP | H05-103697 | A | 4/1993 | |
| JP | H11253199 | A * | 9/1999 | |
| JP | 2002045198 | A | 2/2002 | |
| JP | 3614967 | B2 | 1/2005 | |
| WO | WO-9630503 | A1 * | 10/1996 | C12N 9/96 |

OTHER PUBLICATIONS

Chenault and Whitesides, 1987, "Regeneration of nicotinamide cofactors for use in organic synthesis." Applied biochemistry and biotechnology vol. 14,2: 147-97. (Year: 1987).*
Machine translation of JP_H112534199_A from PE2E (Year: 1999).*
Neeley and Phillipson, 1988, "Automated Enzymatic Method for Determining Ammonia in Plasma, with 14-Day Reagent Stability", Clinical Chemistry, vol. 34, No. 9, pp. 1868-1869 (Year: 1988).*
Druzhinin et al., The photoreduction of nitrogenase, Biochem. J. (1993), vol. 290, pp. 627-631.
Li Xiaoguang Yu et al. ,(Jun. 15, 2012), International Journal of Laboratory Medicine No. 11, pp. 66-68. English Abstract.
International Search Report, European Patent Office, International Patent Application No. PCT/EP2020/052251, Apr. 22, 2020, 7 pages.
Written Opinion of the International Searching Authority, European Patent Office, International Patent Application No. PCT/EP2020/052251, Apr. 22, 2020, 7 pages.
International Preliminary Report on Patentability, The International Bureau of WIPO, International Patent Application No. PCT/EP2020/052251, Jul. 27, 2021, 8 pages.
Chinese Office Action, National Intellectual Property Administration, P. R. China, Chinese Patent Application No. 202080011915.6, Jan. 17, 2025, 3 pages.

(Continued)

*Primary Examiner* — Terry A Mckelvey
*Assistant Examiner* — Andrew T Moehlman
(74) *Attorney, Agent, or Firm* — Taft Stettinius & Hollister LLP

(57) ABSTRACT

The present disclosure deals with the biochemistry of reagents useful in the detection of ammonia in liquid samples. Specifically, the present disclosure is directed to a technical improvement of an enzyme-based test for ammonia that can be used for analysis of plasma samples taken from patients in clinical settings, among other uses. In this regard, stability of a reagent containing NAD(P)H is improved, enhancing shelf life and results in the detection of ammonia. In an exemplary reagent ammonia released as a result of NAD(P)H decay is scavenged using an enzymatic reaction to convert the ammonia using GLDH, NAD(P)H and 2-oxoglutarate, thereby forming L-glutamate, $NAD(P)^+$ and $H_2O$ in the NAD(P)H containing reagent.

10 Claims, 11 Drawing Sheets

(56) References Cited

OTHER PUBLICATIONS

Wen Shaolei, et al., The comparison between two assay modes for determining blood ammonia using automated analyzer, World Health Digest, Medical Monthly No. 10, 3057-3058. Oct. 31, 2007.
Balistreri WF, Rej R., Liver function. In: Burtis CA, Ashwood ER, eds. Tietz Fundamentals of Clinical Chemistry. 4th ed. Philadelphia: WB Saunders 1996;539-569.
Van Anken HC, Schiphorst Me. A kinetic determination of ammonia in plasma. Clin Chim Acta 1974;56:151-157.
Da Fonseca-Wollheim F. Deamidation of glutamine by increased plasma y-glutamyltransferase in a source of rapid ammonia formation in blood and plasma specimens. Clin Chem 1990;36:1479-1482.
Glick MR, Ryder KW, Jackson SA. Graphical Comparisons of Interferences in Clinical Chemistry Instrumentation. Clin Chem 1986;32:470-475.
Breuer J. Report on the Symposium "Drug effects in Clinical Chemistry Methods". Eur J Clin Chem Clin Biochem 1996;34:385-386.
Sonntag O, Scholer A. Drug interference in clinical chemistry: recommendation of drugs and their concentrations to be used in drug interference studies. Ann Clin Biochem 2001;38:376-385.
Bakker AJ, Mücke M. Gammopathy interference in clinical chemistry assays: mechanisms, detection and prevention. Clin Chem Lab Med 2007;45(9):1240-1243.
Da Fonseca-Wollheim F. Direkte Plasmaammoniakbestimmung ohne Enteiweissung. Z Klin Chem Klin Biochem 1973;11:426-431.
Bablok W, Passing H, Bender R, et al. A general regression procedure for method transformation. Application of linear regression procedures for method comparison studies in clinical chemistry, Part III. J Clin Chem Clin Biochem Nov. 1988;26(11):783-790.
Abass et al., Development of an amperometric assay for NH4+ based on a chemically modified screen-printed NADH sensor; Analytica Chimica Acta, vol. 373, No. 1, 1998, pp. 1-8.
CAS SciFinder, 58-68-4; 2021, 9-pages.
CAS SciFinder, 53-59-8; 2021, 5-pages.
Chenault et al., Regeneration of Nicotinamide Cofactors for use in Organic Synthesis, 1987, 51-pages.
Da Fonseca-Wolheim et al., The significance of the hydrogen ion cencetration anbd the addition of ADP in the determination of ammonia with glutamate dehydrogenase; An improved enzymic determination of ammonia, I; Z. Klin. Chem. Klin. Biochem., vol. 11, 1973, 5-pages (translation).
De Ruyck et al., Towards the understanding of the absorption spectra of NAD(P)H/NAD(P)+ as a common indicator of dehydrogenase enzymatic activity; Chemical Physics Letters 450, 2007, pp. 119-122.
Kirsten et al., An enzymatic assay for determination of NH+4, based on the glutamate dehydro-genase reaction, is described. 1963, Biochemische Zeitschrift, vol. 337, pp. 312-319.
Ammonia/Ethanol/CO2 Control N., Roche, 1-page, Jul. 2021.
Ammonia/Ethanol/CO2 Calibrator; Roche, 1-page, Jul. 2021.
NH3 Ammonia; Roche, 4-pages, Jan. 2010.
Ammonia/Ethanol/CO2 Control A; Roche, 1-page, Jul. 2021.
Cat. No. 11877984216 with Cat. Nos. 20751995190, 20752401190, 20753009190, 4 pgs., Jan. 2010.
Cat. No. 20753009190, 1 pg., Jul. 2021.

* cited by examiner

Figure 1
$NADP^+$
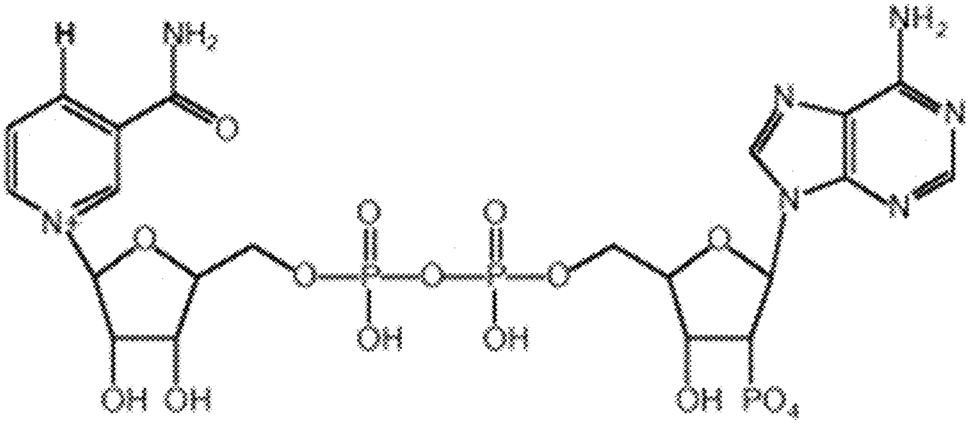
NADPH
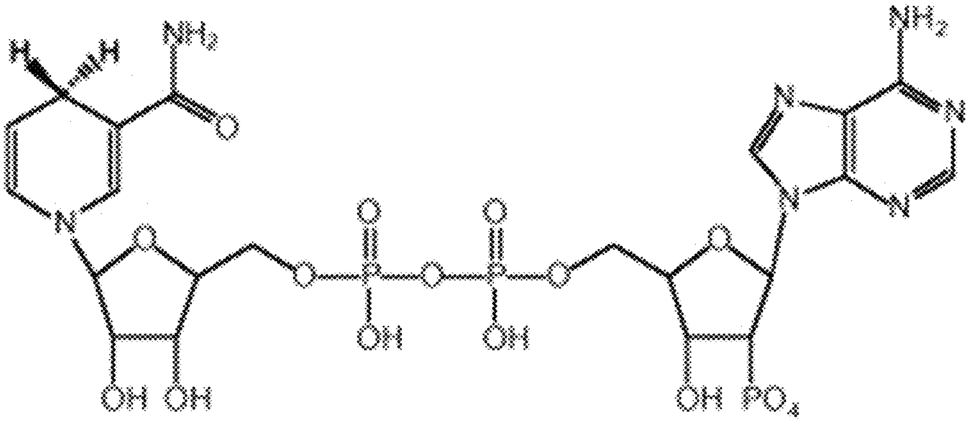

Ammonia II

Order information

| REF | CONTENT | | Analyzer(s) on which **cobas c** pack(s) can be used |
|---|---|---|---|
| **07229593** 190 | Ammonia II (150 tests) | System-ID 07 7606 8 | Roche/Hitachi **cobas c** 311, **cobas c** 501/502 |
| **20751995** 190 | Ammonia/Ethanol/CO2 Calibrator (2 x 4 mL) | Code 688 | |
| **20752401** 190 | Ammonia/Ethanol/CO2 Control Normal (5 x 4 mL) | Code 100 | |
| **20753009** 190 | Ammonia/Ethanol/CO2 Control Abnormal (5 x 4 mL) | Code 101 | |

English

System information

For cobas c 311/501 analyzers:

NH3L2: ACN 479

For cobas c 502 analyzer:

NH3L2: ACN 8479

Intended use

Enzymatic in vitro test for the quantitative determination of ammonia in human plasma on Roche/Hitachi cobas c systems.

Summary

Ammonia is generated primarily in the gastrointestinal tract by metabolism of nitrogenous compounds. An excess of ammonia can be toxic to the central nervous system. The Krebs-Henseleit urea cycle provides a means of disposal of ammonia by metabolizing ammonia to urea in the liver.[1]

Hyperammonemia in infants can be caused by inherited deficiencies of the urea cycle enzymes or acquired through acute (as in Reye's syndrome) or chronic (as in cirrhosis) liver disease. In adults, elevated ammonia levels can aid in diagnosis of liver failure or hepatic encephalopathy from advanced liver diseases such as viral hepatitis or cirrhosis.[1]

Test principle

Enzymatic method, with glutamate dehydrogenase[2]

Glutamate dehydrogenase (GLDH) catalyzes the reductive amination of 2-oxoglutarate with $NH_4^+$ and NADPH to form glutamate and $NADP^+$.

$$NH_4^+ + \text{2-oxoglutarate} + NADPH \xrightarrow{GLDH} \text{L-glutamate} + NADP^+ + H_2O$$

The concentration of the $NADP^+$ formed is directly proportional to the ammonia concentration. It is determined by measuring the decrease in absorbance.

Reagents - working solutions

R1 BICINE[a] buffer: 300 mmol/L, pH 8.3; GLDH (microbial): ≥ 16.7 µkat/L; detergents; preservative

R3 GLDH (microbial): ≥ 5.0 µkat/L; 2-oxoglutarate: 78 mmol/L; NADPH: ≥ 1.3 mmol/L; stabilizer, nonreactive buffer a) BICINE = N,N-bis(2-hydroxyethyl)-glycine R1 is in position B and R3 is in position C.

Precautions and warnings

For in vitro diagnostic use.
Exercise the normal precautions required for handling all laboratory reagents.
Disposal of all waste material should be in accordance with local guidelines.
Safety data sheet available for professional user on request.

This kit contains components classified as follows in accordance with the Regulation (EC) No. 1272/2008:

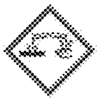

Danger

H318 Causes serious eye damage.

Prevention:

P280 Wear eye protection/ face protection.

Response:

P305 + P351 + P338 + P310 IF IN EYES: Rinse cautiously with water for several minutes. Remove contact lenses, if present and easy to do. Continue rinsing. Immediately call a POISON CENTER/ doctor.

Product safety labeling follows EU GHS guidance.

Contact phone: all countries: +49-621-7590

Reagent handling

Ready for use

Storage and stability

| | |
|---|---|
| Shelf life at 2-8 °C: | See expiration date on **cobas c** pack label. |
| On-board in use and refrigerated on the analyzer: | 16 weeks |

Specimen collection and preparation

For specimen collection and preparation only use suitable tubes or collection containers.

Only the specimens listed below were tested and found acceptable.
$K_2$- and $K_3$-EDTA plasma Pay particular attention that the tubes are adequately filled according to the instruction of the tube manufacturer.

Do not use plasma prepared with other anticoagulants.

Do not use serum since ammonia can be generated during clotting.

The sample types listed were tested with a selection of sample collection tubes that were commercially available at the time of testing, i.e. not all available tubes of all manufacturers were tested. Sample collection systems from various manufacturers may contain differing materials which could affect the test results in some cases. When processing samples in primary tubes (sample collection systems), follow the instructions of the tube manufacturer.

Smoking should be avoided prior to sampling. Tubes should be filled completely and kept tightly stoppered at all times. Place immediately on ice and centrifuge, preferably at 2-8 °C. Perform analysis within 60 minutes of venipuncture or freeze separated plasma immediately.

Ammonia concentrations can increase in vitro due to breakdown of nitrogen-containing plasma components. One known source of ammonia formation is an increased γ-glutamyltransferase activity leading to decomposition of glutamine.[3]

Avoid contamination of samples by ammonia from smoking or traffic in laboratory or patient's room, from glassware or water.

Centrifuge samples containing precipitates before performing the assay.

See the limitations and interferences section for details about possible sample interferences.

| | |
|---|---|
| Stability in plasma: | 30 min at 15-25 °C |
| | 2 hours at 2-8 °C |
| | 3 days at −20 C° ± 5 °C |
| | at least 4 weeks at (−60)-(−80) °C |

Materials provided

See "Reagents – working solutions" section for reagents.

NH3L2
Ammonia II

Figure 3B

Materials required (but not provided)
See "Order information" section
General laboratory equipment

Assay
For optimum performance of the assay follow the directions given in this document for the analyzer concerned. Refer to the appropriate operator's manual for analyzer-specific assay instructions.

The performance of applications not validated by Roche is not warranted and must be defined by the user.

Application for plasma cobas c 311 test definition

| Assay type | 2-Point End |
|---|---|
| Reaction time / Assay points | 10 / 24-57 |
| Wavelength (sub/main) | 546/340 nm |
| Reaction direction | Decrease |
| Units | µmol/L (µg/dL) |

| Reagent pipetting | | Diluent (H₂O) |
|---|---|---|
| R1 | 85 µL | - |
| R3 | 17 µL | 20 µL |

| Sample volumes | Sample | Sample dilution | |
|---|---|---|---|
| | | Sample | Diluent (H₂O) |
| Normal | 17 µL | – | – |
| Decreased | 8.5 µL | – | – |
| Increased | 17 µL | – | – |

cobas c 501/502 test definition

| Assay type | 2-Point End |
|---|---|
| Reaction time / Assay points | 10 / 36-70 |
| Wavelength (sub/main) | 546/340 nm |
| Reaction direction | Decrease |
| Units | µmol/L (µg/dL) |

| Reagent pipetting | | Diluent (H₂O) |
|---|---|---|
| R1 | 85 µL | - |
| R3 | 17 µL | 20 µL |

| Sample volumes | Sample | Sample dilution | |
|---|---|---|---|
| | | Sample | Diluent (H₂O) |
| Normal | 17 µL | – | – |
| Decreased | 8.5 µL | – | – |
| Increased | 17 µL | – | – |

Calibration

| Calibrators | S1: H₂O |
|---|---|
| | It is highly recommended to always use fresh water from closed vessels. |
| | S2: Ammonia/Ethanol/CO2 Calibrator |
| Calibration mode | Linear |
| Calibration frequency | 2-point calibration |
| | - after reagent lot change |
| | - automatically every 2 weeks |
| | - as required following quality control procedures |

Calibration interval may be extended based on acceptable verification of calibration by the laboratory.

Traceability: This method has been standardized against a primary standard.

Quality control
For quality control, use control materials as listed in the "Order information" section. In addition, other suitable control material can be used.

The control intervals and limits should be adapted to each laboratory's individual requirements. Values obtained should fall within the defined limits. Each laboratory should establish corrective measures to be taken if values fall outside the defined limits.

Follow the applicable government regulations and local guidelines for quality control.

Calculation
Roche/Hitachi cobas c systems automatically calculate the analyte concentration of each sample.
Conversion factor: µmol/L × 1.703 = µg/dL.

Limitations - interference
Criterion: Recovery within ± 10 % of initial values at an ammonia concentration of 50 µmol/L.

Icterus:[4] No significant interference up to an I index of 60 for conjugated and unconjugated bilirubin (approximate conjugated and unconjugated bilirubin concentration: 1026 µmol/L or 60 mg/dL).

Hemolysis:[4] No significant interference up to an H index of 100 (approximate hemoglobin concentration: 62.1 µmol/L or 100 mg/dL). Contamination with erythrocytes will elevate results, because the analyte level in erythrocytes is higher than in normal plasma. The level of interference may be variable depending on the content of analyte in the lysed erythrocytes.

Lipemia (Intralipid):[4] No significant interference up to an L index of 700. There is a poor correlation between the L index (corresponds to turbidity) and triglycerides concentration.

Drugs: No interference was found at therapeutic concentrations using common drug panels. Exceptions: Cefoxitin and Intralipid cause artificially high ammonia results at the therapeutic drug level.[5,6]

Physiological plasma concentrations of sulfasalazine may lead to false results.

Temozolomide at therapeutic concentrations may lead to erroneous results.

Drug interferences are measured based on recommendations given in CLSI guidelines EP07 and EP37 and other published literature. Effects of concentrations exceeding these recommendations have not been characterized.

In very rare cases, gammopathy, in particular type IgM (Waldenström's macroglobulinemia), may cause unreliable results.[7]

For diagnostic purposes, the results should always be assessed in conjunction with the patient's medical history, clinical examination and other findings.

ACTION REQUIRED
Special Wash Programming: The use of special wash steps is mandatory when certain test combinations are run together on Roche/Hitachi cobas c systems. The latest version of the carry-over evasion list can be found with the NaOHD-SMS-SmpCln1+2-SCCS Method Sheets. For further instructions refer to the operator's manual. cobas c 502 analyzer: All special wash programming necessary for avoiding carry-over is available via the cobas link; manual input is required in certain cases.

Where required, special wash/carry-over evasion programming must be implemented prior to reporting results with this test.

Limits and ranges
Measuring range
10-1000 µmol/L (17-1703 µg/dL)
Determine samples having higher concentrations via the rerun function. For samples with higher concentrations, the rerun function decreases the sample volume by a factor of 2. The results are automatically multiplied by this factor.
Please consider the recommended sample stability.

NH3L2

Ammonia II

Figure 3C

Lower limits of measurement

*Limit of Blank, Limit of Detection and Limit of Quantitation*

| | |
|---|---|
| Limit of Blank | = 10 µmol/L (17 µg/dL) |
| Limit of Detection | = 10 µmol/L (17 µg/dL) |
| Limit of Quantitation | = 10 µmol/L (17 µg/dL) |

The Limit of Blank, Limit of Detection and Limit of Quantitation were determined in accordance with the CLSI (Clinical and Laboratory Standards Institute) EP17-A2 requirements.

The Limit of Blank is the 95th percentile value from n ≥ 60 measurements of analyte-free samples over several independent series. The Limit of Blank corresponds to the concentration below which analyte-free samples are found with a probability of 95 %.

The Limit of Detection is determined based on the Limit of Blank and the standard deviation of low concentration samples.

The Limit of Detection corresponds to the lowest analyte concentration which can be detected (value above the Limit of Blank with a probability of 95 %).

The Limit of Quantitation is the lowest analyte concentration that can be reproducibly measured with a precision coefficient of variation of ≤ 20 %. It has been determined using low concentration ammonia samples.

Expected values

*EDTA plasma*[5]

| | | |
|---|---|---|
| Women | 11-51 µmol/L | (18.7-86.9 µg/dL) |
| Men | 16-60 µmol/L | (27.2-102 µg/dL) |

Each laboratory should investigate the transferability of the expected values to its own patient population and if necessary determine its own reference ranges.

Specific performance data

Representative performance data on the analyzers are given below. Results obtained in individual laboratories may differ.

Precision

Repeatability and intermediate precision were determined using human samples and controls in accordance with the CLSI (Clinical and Laboratory Standards Institute) EP5-A3 requirements (2 aliquots per run, 2 run per day, 21 days). The following results were obtained:

| *Repeatability* | *Mean* µmol/L (µg/dL) | *SD* µmol/L (µg/dL) | *CV* % |
|---|---|---|---|
| AEC Control N[b] | 66.6 (113) | 1.40 (2.38) | 2.1 |
| AEC Control A[c] | 243 (414) | 3.45 (5.88) | 1.4 |
| Human plasma 1 | 26.0 (44.3) | 1.26 (2.15) | 4.8 |
| Human plasma 2 | 57.7 (98.3) | 1.63 (2.78) | 2.8 |
| Human plasma 3 | 110 (187) | 1.62 (2.76) | 1.5 |
| Human plasma 4 | 492 (838) | 4.12 (7.02) | 0.8 |
| Human plasma 5 | 863 (1470) | 9.54 (16.2) | 1.1 |

| *Intermediate precision* | *Mean* µmol/L (µg/dL) | *SD* µmol/L (µg/dL) | *CV* % |
|---|---|---|---|
| AEC Control N[b] | 67.9 (116) | 1.61 (2.74) | 2.4 |
| AEC Control A[c] | 243 (414) | 4.26 (7.25) | 1.8 |
| Human plasma 1 | 26.0 (44.3) | 1.29 (2.20) | 4.9 |
| Human plasma 2 | 57.7 (98.3) | 1.72 (2.93) | 3.0 |
| Human plasma 3 | 110 (187) | 1.92 (3.27) | 1.7 |
| Human plasma 4 | 480 (817) | 6.30 (10.7) | 1.3 |
| Human plasma 5 | 853 (1453) | 12.4 (21.1) | 1.5 |

b) Ammonia/Ethanol/CO2 Control Normal
c) Ammonia/Ethanol/CO2 Control Abnormal

Method comparison

Ammonia values for human plasma samples obtained on a Roche/Hitachi cobas c 501 analyzer (y) were compared with those determined using the AMM reagent of Beckman Coulter on a Beckman Synchron DxC 800 analyzer (x).

Sample size (n) = 111

| Passing/Bablok[9] | Linear regression |
|---|---|
| y = 1.002x − 2.01 µmol/L | y = 1.020x − 4.88 µmol/L |
| τ = 0.979 | r = 1.000 |

The sample concentrations were between 17.0 and 984 µmol/L (29.0 and 1676 µg/dL).

References

1. Balistreri WF, Rej R. Liver function. In: Burtis CA, Ashwood ER, eds. Tietz Fundamentals of Clinical Chemistry. 4th ed.Philadelphia: WB Saunders 1996;539-568.
2. Van Anken HC, Schiphorst ME. A kinetic determination of ammonia in plasma. Clin Chim Acta 1974;56:151-157.
3. Da Fonseca-Wollheim F. Deamidation of glutamine by increased plasma γ-glutamyltransferase is a source of rapid ammonia formation in blood and plasma specimens. Clin Chem 1990;36:1479-1482.
4. Glick MR, Ryder KW, Jackson SA. Graphical Comparisons of Interferences in Clinical Chemistry Instrumentation. Clin Chem 1986;32:470-475.
5. Breuer J. Report on the Symposium "Drug effects in Clinical Chemistry Methods". Eur J Clin Chem Clin Biochem 1996;34:385-386.
6. Sonntag O, Scholer A. Drug interference in clinical chemistry: recommendation of drugs and their concentrations to be used in drug interference studies. Ann Clin Biochem 2001;38:376-385.
7. Bakker AJ, Mücke M. Gammopathy interference in clinical chemistry assays: mechanisms, detection and prevention. Clin Chem Lab Med 2007;45(9):1240-1243.
8. Da Fonseca-Wollheim F. Direkte Plasmaammoniakbestimmung ohne Enteiweissung. Z Klin Chem Klin Biochem 1973;11:426-431.
9. Bablok W, Passing H, Bender R, et al. A general regression procedure for method transformation. Application of linear regression procedures for method comparison studies in clinical chemistry, Part III. J Clin Chem Clin Biochem 1988 Nov;26(11):783-790.

A point (period/stop) is always used in this Method Sheet as the decimal separator to mark the border between the integral and the fractional parts of a decimal numeral. Separators for thousands are not used.

Symbols

Roche Diagnostics uses the following symbols and signs in addition to those listed in the ISO 15223-1 standard (for USA: see https://usdiagnostics.roche.com for definition of symbols used):

| | |
|---|---|
| CONTENT | Contents of kit |
| → | Volume after reconstitution or mixing |
| GTIN | Global Trade Item Number |

COBAS and COBAS C are trademarks of Roche.
All other product names and trademarks are the property of their respective owners.
Additions, deletions or changes are indicated by a change bar in the margin.
© 2018, Roche Diagnostics

STABILIZATION OF NADPH OR NADH IN AMMONIA DETECTION ASSAYS

This application is a national phase application of International Application No. PCT/EP2020/052251 filed Jan. 30, 2020, which claims priority to European Application No. 19154870.0 filed Jan. 31, 2019, the disclosures of which are hereby incorporated by reference in their entirety.

The present disclosure deals with the biochemistry of reagents useful in the detection of ammonia in liquid samples. Specifically, the present disclosure is directed to a technical improvement of an enzyme-based test for ammonia that can be used for analysis of plasma samples taken from patients in clinical settings, among other uses. In this regard, stability of a reagent containing NAD(P)H is improved, enhancing shelf life and results in the detection of ammonia. In an exemplary reagent ammonia released as a result of NAD(P)H decay is scavenged using an enzymatic reaction to convert the ammonia using GLDH (glutamate dehydrogenase), NAD(P)H and 2-oxoglutarate, thereby forming L-glutamate, $NAD(P)^+$ and $H_2O$ in the NAD(P)H containing reagent

BACKGROUND OF THE INVENTION

In higher animals and particularly in humans, ammonia is generated primarily in the gastrointestinal tract by metabolism of nitrogenous compounds. An excess of ammonia can be toxic to the central nervous system. The Krebs-Henseleit urea cycle provides a means of disposal of ammonia by metabolizing ammonia to urea in the liver. Hyperammonemia in human infants can be caused by inherited deficiencies of the urea cycle enzymes or acquired through acute (as in Reye's syndrome) or chronic (as in cirrhosis) liver disease. In human adults, elevated ammonia levels can aid in diagnosis of liver failure or hepatic encephalopathy from advanced liver diseases such as viral hepatitis or cirrhosis. Thus, ammonia is a significant clinical parameter, and in vitro assays for ammonia are technically desired.

In 1963, Kirsten et al. introduced an enzymatic method for ammonia determination based on the action of glutamate dehydrogenase (Kirsten E, et al. Biochem Z 337 (1963) 312-319). Although the enzymatic method proved to be highly specific and utilized direct evaluation based on the molar absorptivity of NADH, several problems, including difficulties in stabilizing the end reaction, were encountered.

An improvement of this technical approach is Da Fonseca-Wollheim's modification of the Kirsten reaction. The original enzymatic method is improved by the addition of ADP to the reaction mixture, the use of NADPH in place of NADH to eliminate interference from the reaction of endogenous LDH with endogenous pyruvate, and the substitution of plasma for deproteinized supernatant (Da Fonseca-Wollheim F. Z Klin Chem Klin Biochem 11 (1973) 421-425).

JP03614967B2 discloses removal of ammonium from a specimen effected using a combination comprising 2-oxoglutarate, GLDH, glucose-6-phosphate, glucose-6-phosphate dehydrogenase and NADPH.

Chenault K. H & Whitesides G. M Appl Biochem Biotechnol. 14 (1987) 147-197 report different approaches for regeneration of nicotinamide cofactors.

An exemplary embodiment of Da Fonseca-Wollheim's modification in the field of clinical chemistry and in vitro diagnostics is the Cobas® $NH_3$ (Ammonia) assay kit for Roche/Hitachi analyzers (including the MODULAR P, cobas c platforms; e.g. Roche Cat. No. 11877984216 with Cat. Nos. 20751995190, 20752401190, 20753009190 as calibrators), for quantitative determination of ammonia in blood plasma. The kit in use comprises a reagent container with a first and a second aqueous working solution, also referred to as R1 and R2.

The assay principle makes use of a reaction that is catalyzed by glutamate dehydrogenase (GLDH), EC 1.4.1.3. In aqueous solution GLDH catalyzes reductive amination of 2-oxoglutarate with $NH_4^+$ and the co-substrate NADPH, thereby forming glutamate and $NADP^+$. In the course of the diagnostic assay workflow the plasma sample is mixed with an aliquots of R1 and R2, and incubated. After incubation the amount of oxidized co-substrate $NADP^+$ is determined photometrically by measuring the difference absorbance for NADPH before and after adding the sample, and the corresponding amount of ammonia in the sample is determined using calibration data which are gathered in separate measurements.

In order to ensure stability and shelf life of the reactive compounds involved, the aqueous solutions thereof need to be kept under adequate conditions. Specifically, GLDH becomes increasingly unstable with increasing pH. For the purpose of a diagnostic assay GLDH is technical not practical if stored under alkaline conditions above pH 10. However, a pH lower than pH 9 allows for sufficient stability, shelf life and usability of GLDH. Thus, in the exemplary Cobas® $NH_3$ (Ammonia) assay kit, the working solution R1 is an aqueous solution buffered at pH 8.3 (i.e. lower than pH 9) which is provided by the manufacturer as a ready to use liquid reagent in the commercially available assay kit.

In contrast, NADPH (and similarly NADH) is sufficiently stable in solution at a pH above pH 10. But nevertheless, over time NAD(P)H exhibits decay in aqueous solution, even at a pH above pH 10. To deal with this instability, the Cobas® $NH_3$ (Ammonia) assay kit is shipped with dry ingredients of R2 including NADPH. When kept as dry matter NADPH remains stable. Prior to use the R2 working solution is prepared by dissolving the dry NADPH an aqueous buffer, thereby forming the aqueous solution (R2) which is ready for subsequent (and preferably immediate) consumption in the diagnostic assay workflow to determine $NH_3$ in the sample. As this requires extra manual work, a stabilized ready-to-use reagent with NADPH is desired.

As a result of NADPH decay ammonia is formed as a product. For this particular reason, there is a technical need to counteract NADPH decay in reagents for use in an assay to determine and quantify ammonia in a sample. Thus, over time $NH_3$ accumulates in an R2 working solution due to NADPH decay, with the risk of causing falsely elevated measurement values The compositions, kits methods and uses described in the present disclosure are designed to provide improvements in view of the technical needs mentioned above. Based on the teachings as detailed herein, assays for the determination of ammonia in liquid samples can be advantageously improved. Surprisingly the shelf life of a NAD(P)H containing aqueous reagent can be prolonged, even under harsh conditions.

SUMMARY OF THE INVENTION

Herein is reported as a first aspect which is related to all other aspects and embodiments of the present disclosure an assay kit for quantitatively determining the concentration of ammonia in an aqueous liquid sample, the kit containing 2-oxoglutarate, glutamate dehydrogenase capable of reacting NAD(P)H as a co-substrate (=GLDH), and NAD(P)H, wherein the kit comprises a first and a second container, wherein the first container contains a first aqueous reagent with a first amount of GLDH, the first reagent having a pH capable of maintaining enzymatic activity of GLDH, wherein the second container contains a second aqueous reagent with NAD(P)H, 2-oxoglutarate, and a second amount of GLDH, wherein the GLDH enzymatic activity per mL of the first reagent is higher than the GLDH enzymatic activity per mL reagent in the second reagent, and wherein the pH of the second reagent is capable of maintaining enzymatic activity of GLDH in the second reagent to convert ammonia, NAD(P)H and 2-oxoglutarate thereby being able of forming L-glutamate, $NAD(P)^+$ and $H_2O$ in the second reagent.

Herein is reported as a second aspect which is related to all other aspects and embodiments of the present disclosure a method to provide an assay kit for quantitatively determining the concentration of ammonia in an aqueous liquid sample, the kit comprising two different aqueous reagents, the reagents containing in aqueous solution 2-oxoglutarate, glutamate dehydrogenase capable of reacting NAD(P)H as a co-substrate (=GLDH), and NAD(P)H, the method comprising the steps of preparing a first reagent by dissolving GLDH in an aqueous solution with a pH capable of maintaining enzymatic activity of GLDH, preparing a second reagent by dissolving in an aqueous solution 2-oxoglutarate, GLDH, and NAD(P)H, and adjusting the pH of the second reagent to be permissive for maintaining enzymatic activity of GLDH in the second reagent to convert ammonia, NAD(P)H, and 2-oxoglutarate, thereby allowing formation of L-glutamate, $NAD(P)^+$ and $H_2O$ in the second reagent, providing the first and the second reagent in separate containers, and combining the containers in a kit of parts, thereby providing an assay kit for quantitatively determining the concentration of ammonia in an aqueous liquid sample.

Herein is reported as a third aspect which is related to all other aspects and embodiments of the present disclosure the use of an assay kit according to the first aspect or an assay kit obtained from practicing the method of the second aspect, for quantitatively determining the concentration of ammonia in an aqueous liquid sample.

Herein is reported as a fourth aspect which is related to all other aspects and embodiments of the present disclosure an assay kit according to the first aspect or an assay kit obtained from practicing the method of the second aspect, wherein the concentration of ammonia in the second reagent is about 1.5 μM or less, more specifically from about 0.01 μM to about 1.5 μM.

Herein is reported as a fifth aspect which is related to all other aspects and embodiments of the present disclosure a mixture comprising (i) an aqueous liquid sample suspected of containing ammonia, and (ii) the second reagent of the assay kit, including an assay kit according to the first aspect or an assay kit obtained from practicing the method of the second aspect.

Herein is reported as a sixth aspect which is related to all other aspects and embodiments of the present disclosure an automated device capable of forming a mixture according to the fifth aspect, wherein the device is combined with (i) an aqueous liquid sample in a sample container and (ii) an assay kit according to the first aspect or an assay kit obtained from practicing the method of the second aspect.

DETAILED DESCRIPTION OF THE INVENTION

The terminology used herein is for the purpose of describing particular embodiments only and is not intended to be limiting of the invention.

In this detailed description, references to "one embodiment", "an embodiment", or "in embodiments" mean that the feature being referred to is included in at least one embodiment of the technology with regards to all its aspects according to present disclosure. Moreover, separate references to "one embodiment", "an embodiment", or "embodiments" do not necessarily refer to the same embodiment; however, neither are such embodiments mutually exclusive, unless so stated, and except as will be readily apparent to those skilled in the art. Thus, the technology in all its aspects according to present disclosure can include any variety of combinations and/or integrations of the embodiments described herein.

The terms "a", "an" and "the" generally include plural referents, unless the context clearly indicates otherwise. As used herein, "plurality" is understood to mean more than one. For example, a plurality refers to at least two, three, four, five, or more. Unless specifically stated or obvious from context, as used herein, the term "or" is understood to be inclusive.

It is further understood that the root terms "include" and/or "have", when used in this specification, specify the presence of stated features, items, integers, steps, operations, elements, and/or components, but do not preclude the presence or addition of at least one other feature, integer, step, operation, element, component, and/or groups thereof. In an analogous way, "with" also specify the presence of stated features, etc.

As used herein, the terms "comprises," "comprising,", "contains", "containing", "includes," "including," "has," "having" or any other variation thereof, are intended to cover a non-exclusive inclusion, i.e. indicate an open list of features. For example, a process, method, article, or apparatus that comprises a list of features is not necessarily limited only to those features but may include other features not expressly listed or inherent to such process, method, article, or apparatus. In contrast, "consists of", "consisting of" or any other variation thereof specify a closed list of features. Notably, the closed list of given features is understood as representing a specific embodiment of an open list of these features.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

As used herein "substantially", "relatively", "generally", "typically", and "approximately" are relative modifiers intended to indicate permissible variation from the characteristic so modified. They are not intended to be limited to the absolute value or characteristic which it modifies but rather approaching or approximating such a physical or functional characteristic. Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

"Ammonia" is a well-known compound of nitrogen and hydrogen with the formula $NH_3$. It can be dissolved in water, the aqueous solution of ammonia is alkaline. Ammonia is a base with a base constant $pK_b$ of 4.76. Thus, in aqueous solution an amount of the ammonia molecules react with water molecules to yield ammonium ions (="ammonium")

and hydroxyl ions. It is understood that to the extent that there is ammonia in an aqueous solution, it is in reaction equilibrium with ammonium, unless explicitly stated otherwise.

2-Oxoglutaric acid (=α-ketoglutaric acid) is one of two ketone derivatives of glutaric acid. Its anion, 2-oxoglutarate (=α-ketoglutarate) is an important biological compound. It is the keto acid produced by deamination of glutamate, and is an intermediate in the Krebs cycle.

Glutamate dehydrogenase (=GLDH) is an enzyme, present in most microbes and the mitochondria of eukaryotes. GLDH activity is capable of converting L-glutamate to α-ketoglutarate, and vice versa. It is understood that all aspects and embodiments of the present report relate to GLDH (EC 1.4.1.3) that is capable of reacting NAD(P)H as a co-substrate.

Nicotinamide adenine dinucleotide (NAD$^+$) and nicotinamide adenine dinucleotide phosphate (NADP$^+$) are co-substrates of GLDH. They are composed of an AMP (adenosine monophosphate) molecule covalently linked to a nicotinamide mononucleotide, hence dinucleotide. NADP$^+$ differs from NAD$^+$ by the presence of an additional phosphate group on carbon two of the ribose ring of AMP. These molecules are diffusible cosubstrates that take part in oxidation/reduction (=redox) reactions. NAD$^+$ and NADP$^+$ are the oxidized forms of the respective cosubstrate. When reduced, carbon four of the nicotinamide ring accepts a hydride (H$^-$) ion, a proton and two electrons. NAD+/ NADP+ always undergo two electron oxidations or reductions. NADH and NADPH are the abbreviation for the reduced forms. With respect to GLDH enzymatic activity, not only NADH and NADPH can serve as substrates, but also functional analogs thereof. In FIG. 4A-H several of these are illustrated. For the purpose of the present report it is herewith stated that the teachings as described thein in all aspects and embodiments can advantageously also be practiced with any of the functional analogs, provided that the particular GLDH in use is capable of reacting the reduced form of the respective functional analog in a redox reaction with 2-oxoglutarate, thereby producing the oxidized form of the functional analog.

For the purpose of the present disclosure, an "assay kit" is understood as a composition of parts which are combined for the purpose of performing an assay. Typically, the assay involves detection and determination (quantification) of an analyte in a sample, such as but not limited to the analyte ammonia in plasma as the material of the sample. Importantly, the meaning of "assay kit" denotes the composition of parts prior to use which exhausts one or more parts comprised in the kit. In the specific embodiment of a container which encases (contains) a liquid reagent it is understood that prior to use the container is closed and optionally sealed. Prior to use of the container is opened wherein the seal, if present, is broken. Aspects and embodiments reported in the present disclosure are directed to an assay kit as a kit of parts comprising at least two parts, part A and part B. Other parts may be present in an assay kit according to the present disclosure. Each part typically comprises one or more components. When providing the kit of parts it should—if possible—be avoided to combine components within a part, components, which may chemically react with each other thereby forming an undesired product, especially during storage of the kit of parts. Thus, the kit of parts typically is provided in a manner, where those reactive components are separated from each other, at least during storage in order to avoid an undesired reaction. While the technical problem posed by undesired reactions of NAD(P)H is dealt with specifically, it is understood that all other components in parts of an assay kit as disclosed herein are in an appropriate environment, e.g. (not limiting) reagents are enclosed in a casing (container) which protects against evaporation of liquids, enzymes and substrates are provided in solvents composed to be permissive for use according to the purpose of the assay kit, and other art-accepted measures. An assay kit also typically comprises packaging material and either a document with information concerning intended use of the assay kit and recommended or required conditions of storage prior to use of the kit. With regards to the packaging material a specific embodiment thereof allows the user to recognize a kit which has been opened already and therefore may not be in the original condition after manufacture, e.g. by a seal of originality.

The findings reported in the present disclosure on the one hand relate to Da Fonseca-Wollheim's modification of the Kirsten reaction. The original enzymatic method is improved by the addition of ADP to the reaction mixture, the use of NADPH in place of NADH to eliminate interference from the reaction of endogenous LDH with endogenous pyruvate, and the substitution of plasma for deproteinized supernatant (Da Fonseca-Wollheim F. Z Klin Chem Klin Biochem 11 (1973) 421-425). On the other hand, however, the findings of the present disclosure more generally relate to stabilization of aqueous solutions of NADPH and NADH, specifically for the purpose of determining ammonia, wherein relevant detection assays are based on the enzymatic activity of glutamate dehydrogenase.

Typically, detection reagents specific for ammonia are selected and designed to be capable of simultaneously
    i) quantitatively reacting the ammonium (and therefore the ammonia being in a reaction equilibrium with ammonium, in aqueous solution) that is present in the sample, and
    ii) producing a detectable reaction product in stoichiometric amounts reflecting the amount of reacted ammonia.

A long-established assay principle makes use of the following reaction [Reaction 1] that is catalyzed by glutamate dehydrogenase (GLDH). In aqueous solution GLDH catalyzes the reductive amination of 2-oxoglutarate with NH$_4^+$ and NADPH, thereby forming glutamate and NADP$^+$.

[Reaction 1]

$$NH_4^+ \ + \ \text{2-oxoglutarate} \ + \ NADPH \ \xrightarrow{\text{GLDH}} \ \text{L-glutamate} \ + \ NADP^+ \ + \ H_2O$$

The co-substrate in [Reaction 1] is NADPH being the reduced form of nicotinamide adenine dinucleotide phosphate (CAS No. 53-59-8); the corresponding oxidized form is NADP$^+$. Alternatively, the co-substrate can be NADH being the reduced form of nicotinamide adenine dinucleotide (CAS No. 58-68-4); the corresponding oxidized form is NAD$^+$. The alternative enzymatic reaction is analogous as follows [Reaction 2].

[Reaction 2]

$$NH_4^+ \ + \ \text{2-oxoglutarate} \ + \ NADH \ \xrightarrow{\text{GLDH}} \ \text{L-glutamate} \ + \ NAD^+ \ + \ H_2O$$

As already mentioned above, to the extent that there is ammonia in an aqueous solution, it is in reaction equilibrium with ammonium, unless explicitly stated otherwise. For the purpose of the present disclosure, any of [Reaction 1] and

[Reaction 2], either alone or combined are also referred to as "detection reaction". In addition, any of NADPH and NADH c are also referred to as "reduced co-substrate". Further, any of $NADP^+$ and $NAD^+$ are also referred to as "oxidized co-substrate".

Importantly, both detection reactions yield the respective oxidized co-substrate in stoichiometric amounts, thus reflecting the amount of reacted ammonium. The co-substrates strongly absorb ultraviolet light, and the difference between a reduced and an oxidized co-substrate can be detected photometrically. Thus, the difference in the absorption spectra between the oxidized and reduced forms of the co-substrate makes it simple to measure this conversion in enzyme assays of [Reaction 1] or [Reaction 2].

Therefore, with great advantage NADH and NADPH are used as co-substrates in a multitude of quantitative assays which are based on enzyme-catalyzed redox reactions, and specifically such assays to assess concentrations of ammonia in liquid aqueous samples. There is a stoichiometric relationship in that for each enzyme-catalyzed redox reaction involving one ammonium ion there is one NAD(P)H molecule converted to $NAD(P)^+$. Spectrophotometric measurement allows to quantitatively detect any changes of the initial amount of NADH or NADPH initially present in the reaction. With regards to [Reaction 1] and [Reaction 2], by way of detectably forming the respective oxidized form as reaction product in stoichiometric amounts, spectrophotometric measurement of the respective oxidized form reflects the amount of ammonium (and ammonia) reacted. The co-substrate and the acceptor compound 2-oxoglutarate are present in molar excess, the chemical equilibrium is shifted toward the product side (L-glutamate+$NAD(P)^+$+$H_2O$). As a result, all available ammonia is eventually converted, that is to say reacted quantitatively, thereby giving rise to an equivalent molar amount of $NAD^+$ or $NADP^+$, respectively.

NAD(P)H molecules in aqueous solution are instable, i.e. show a tendency to decay, thereby releasing ammonia. Example 3 lists in Table 1 the experiments ##1, 3, 4 and 5 which illustrate that ammonia release with time is indeed the case for aqueous solutions of NAD(P)H. The technical problem arising with such ammonia releasing decay of the co-substrate is specifically evident in cases where an aqueous solution of NAD(P)H is to be used as a reagent in the detection of ammonia in a sample. The lower the ammonia concentration in the sample, the more severe the risk posed by the NAD(P)H containing aqueous reagent is, in view of possible falsely elevated quantitative measurements of ammonia.

However it could be shown by the inventors, and is documented in the present disclosure, that even under conditions which are less than suboptimal (especially at a pH higher than 9, or even higher) a certain proportion of GLDH retains activity, in the presence of 2-oxoglutarate and NAD (P)H. The impact of this finding can be exemplified, in a non-limiting way, by the Roche Diagnostics Cobas® $NH_3$ diagnostic assay. The present Cobas® $NH_3$ assay uses two different reagents, R1 and R2 which are mixed with the sample that is suspected to contain ammonia. R1 contains 2-oxoglutarate as a ready made liquid reagent. Just before use, R2 is to be prepared freshly from solid material and aqueous solutions, and after the preparation is complete contains NADPH, GLDH and 2-oxoglutarate. Thus, the presently available Cobas® $NH_3$ diagnostic assay kit does not contain two ready-to-use assay reagents but only one. The kit contains further bottles with liquid contents and solid material from which the R2 reagent is to be prepared manually prior to use.

So a first aspect which is related to all other aspects and embodiments of the present disclosure is an assay kit for quantitatively determining the concentration of ammonia in an aqueous liquid sample, the kit containing 2-oxoglutarate, glutamate dehydrogenase capable of reacting NAD(P)H as a co-substrate (=GLDH), and NAD(P)H, wherein the kit comprises a first and a second container, wherein the first container contains a first aqueous reagent with a first amount of GLDH, the first reagent having a pH capable of maintaining enzymatic activity of GLDH, wherein the second container contains a second aqueous reagent with NAD(P) H, 2-oxoglutarate, and a second amount of GLDH, wherein the GLDH enzymatic activity per mL of the first reagent is higher than the GLDH enzymatic activity per mL reagent in the second reagent, and wherein the pH of the second reagent is capable of maintaining enzymatic activity of GLDH in the second reagent to convert ammonia, NAD(P)H and 2-oxoglutarate thereby being able of forming L-glutamate, $NAD(P)^+$ and $H_2O$ in the second reagent.

It is important to appreciate that nor the first neither the second reagent in the assay kit as provided here requires a separate manual preparation step prior to use. Thus, in an embodiment of the assay kit, the kit may comprise (more specifically comprises) only two containers with two aqueous solutions, wherein any of the two solutions includes one or more compounds selected from NAD(P)H, GLDH and 2-oxoglutarate. In an embodiment NAD(P)H is present only in the second reagent.

In an embodiment the pH of the first reagent is from pH 7 to pH 9, and more specifically between pH 8 and pH 9. Specific embodiments are pH values of the first reagent, wherein a particular value is selected from 8.5 to 8.9.

Concerning the second reagent in particular, a central finding which is basis of the present report is that, for the purpose of scavenging ammonia from the NAD(P)H containing reagent, GLDH can be used under conditions which were thought to be technically unfit for use. Thus, conditions can be selected for the NAD(P)H reagent which mostly favour stability of NAD(P)H, i.e. reduce the tendency to release ammonia. Moreover, the presence of the GLDH enzyme keeps the reagent free from ammonia. An important factor in this context is the pH of the reagent which is selected to be substantially alkaline. Thus, in an embodiment the pH of the second reagent is from pH 8 to pH 11, and more specifically between pH 8 and pH 10, even more specifically between pH 9 and pH 10.

Example 2 illustrates in a non-limiting way that the newly developed Cobas® $NH_3L2$ R1 reagent provides the larger portion of GLDH enzymatic activity, to be used for ammonia detection in the sample. Notably, the R1 reagent does not contain 2-oxoglutarate. This is an example for an embodiment in which 2-oxoglutarate is present only in the second reagent.

The newly developed second (R3) reagent contains the lesser portion of GLDH, however enough to uphold the ammonia scavenging mechanism. Thus, in an embodiment the ratio between the GLDH enzymatic activity per mL present in the first reagent and the GLDH enzymatic activity per mL present in the second reagent is from 15:1 to 1.5:1, more specifically from 10:1 to 2:1, even more specifically from 5:1 to 2:1, even more specifically the ratio is about 3:1. In another embodiment, relative to the total GLDH enzymatic activity provided by the reagents comprised in the kit the second reagent contains an amount of GLDH enzymatic activity form 1% to 30%, the amount being more specifically selected from any of 2% to 5%, 5% to 7%, 7% to 10%, 10% to 15%, 15% to 20%, 20% to 25%, and 25% to 30%.

The above description of embodiments concerning the first aspect are equally applicable for the second aspect, and the other aspects, too. Thus, a second aspect which is related to all other aspects and embodiments of the present disclosure is a method to provide an assay kit for quantitatively determining the concentration of ammonia in an aqueous liquid sample, the kit comprising two different aqueous reagents, the reagents containing in aqueous solution 2-oxoglutarate, glutamate dehydrogenase capable of reacting NAD(P)H as a co-substrate (=GLDH), and NAD(P)H, the method comprising the steps of preparing a first reagent by dissolving GLDH in an aqueous solution with a pH capable of maintaining enzymatic activity of GLDH, preparing a second reagent by dissolving in an aqueous solution 2-oxoglutarate, GLDH, and NAD(P)H, and adjusting the pH of the second reagent to be permissive for maintaining enzymatic activity of GLDH in the second reagent to convert ammonia, NAD(P)H, and 2-oxoglutarate, thereby allowing formation of L-glutamate, $NAD(P)^+$ and $H_2O$ in the second reagent, providing the first and the second reagent in separate containers, and combining the containers in a kit of parts, thereby providing an assay kit for quantitatively determining the concentration of ammonia in an aqueous liquid sample.

The third aspect which is related to all other aspects and embodiments of the present disclosure relates to the use of an assay kit according to the first aspect or an assay kit obtained from practicing the method of the second aspect, for quantitatively determining the concentration of ammonia in an aqueous liquid sample.

Another remarkable advantage of the technology presented in this report is increased shelf life and enhanced stability of a reagent that is manufactured as an aqueous solution and contains NAD(P)H, in view of contamination of ammonia by decomposition of the co-substrate. Thus the fourth aspect which is related to all other aspects and embodiments of the present disclosure relates an assay kit according to the first aspect or an assay kit obtained from practicing the method of the second aspect, wherein the concentration of ammonia in the second reagent is about 1.5 μM or less, more specifically from about 0.01 μM to about 1.5 μM.

In a fifth aspect which is related to all other aspects and embodiments of the present disclosure provides a mixture comprising (i) an aqueous liquid sample suspected of containing ammonia, and (ii) the second reagent of the assay kit, including an assay kit according to the first aspect or an assay kit obtained from practicing the method of the second aspect. In a specific example the amount of ammonia from the second reagent which adds to the amount of ammonia present in the sample is about 1.5 μM or less.

Herein is reported as a sixth aspect which is related to all other aspects and embodiments of the present disclosure an automated device capable of forming a mixture according to the fifth aspect, wherein the device is combined with (i) an aqueous liquid sample in a sample container and (ii) an assay kit according to the first aspect or an assay kit obtained from practicing the method of the second aspect. In an embodiment related to all other aspects and embodiments the assay kit comprises a reagent cassette, wherein the reagent cassette comprises at least a first and a second sealed compartment, wherein the first compartment is the first container according to the above given first aspect, and the second compartment is the second container, accordingly. Thus, in an embodiment related to all aspects and embodiments as provided herein, there is provided an assay kit of the first aspect, wherein the first and the second container are combined in any of a holder, a rack and a cassette, wherein the openings of the first and second containers are closed and sealed. Thereby any user is enabled to recognize whether or not the solutions are in their original state after manufacture. In a more specific embodiment the first and the second container are combined in a Cobas® reagent cassette compatible with any of the Roche Diagnostics Cobas® c platforms c 311, c 501/502, and c 701/702. In this embodiment the reaction cassette provides separate compartments which function as first and second container as provided herein.

The following examples and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 1 Chemical formulas of $NADP^+$ and NADPH

FIG. 3A-C Depiction of working instructions for an improved diagnostic assay for ammonia detection and quantification, according to the teachings of the present report.

EXAMPLE 1

Figure 2:
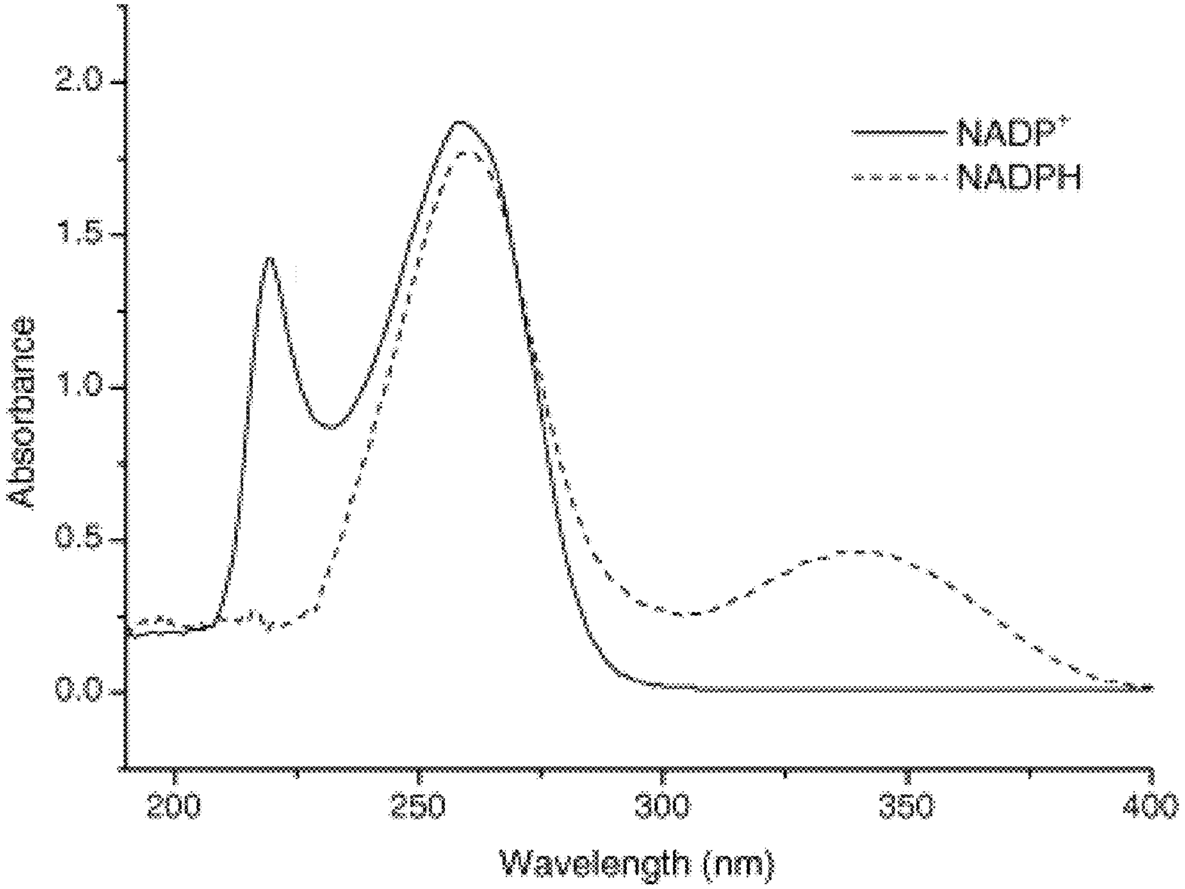
FIG. 2 Experimental UV/vis spectra of $NADP^+$ and NADPH as reported in De Ruyck J. et al. Chem Phys Lett 450 (2007) 119-122.
Figure 4A:
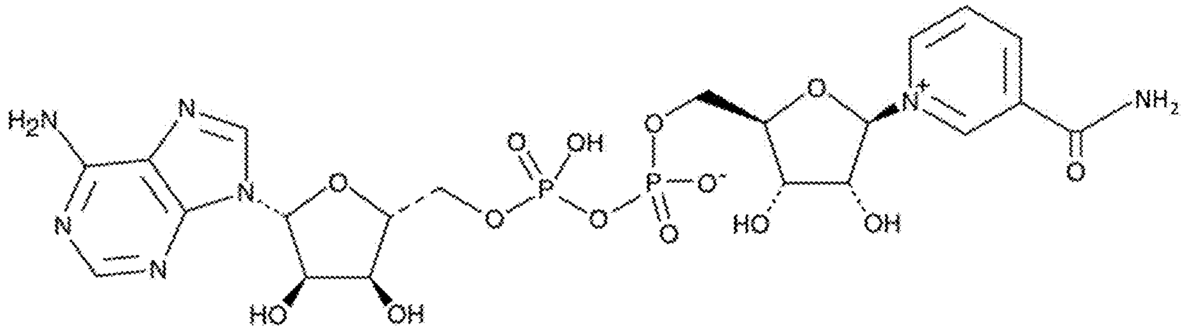
FIG. 4A-H Depiction of the molecular structures of oxidized forms of co-substrates for GLDH: (A) $NAD^+$, (B) $NADP^+$, (C) 3-Acetylpyridine-$NAD^+$, (D) 3-Acetylpyridine-$NADP^+$, (E) 3-Pyridinealdehyde-$NAD^+$, (F) 3-Pyridinealdehyde-$NADP^+$, (G) Thionicotineamide-$NAD^+$, (H) Thionicotineamide-$NADP^+$.
Figure 4B:
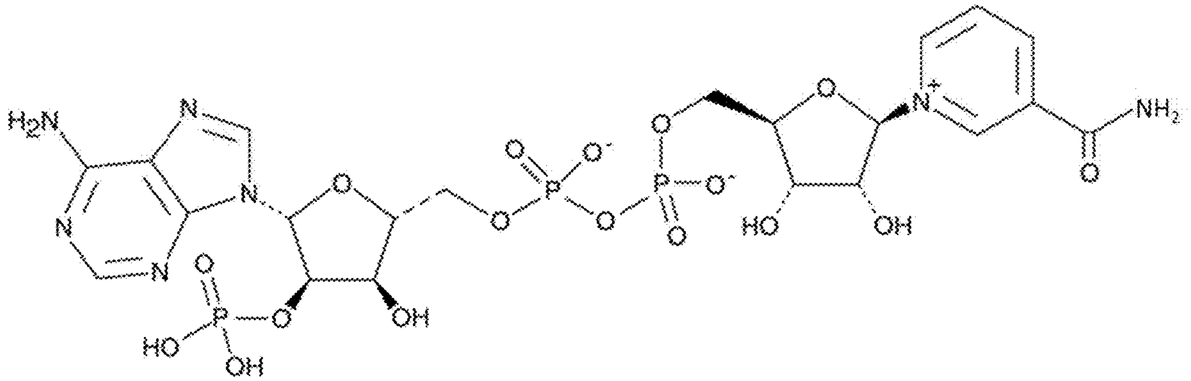
Figure 4C:
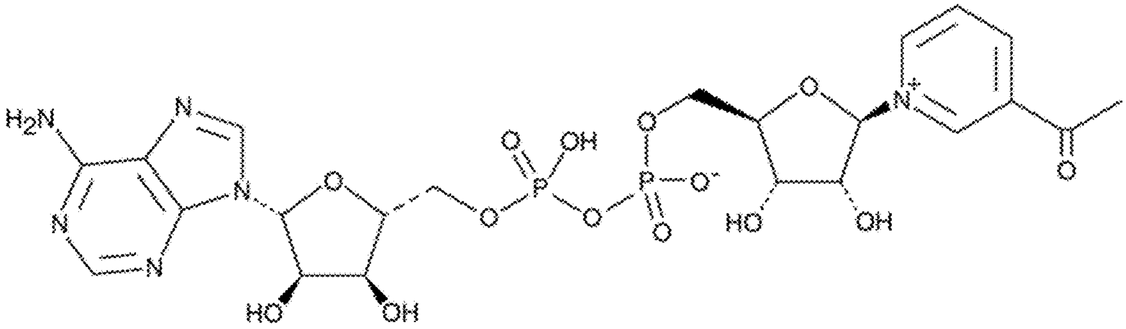
Figure 4D:
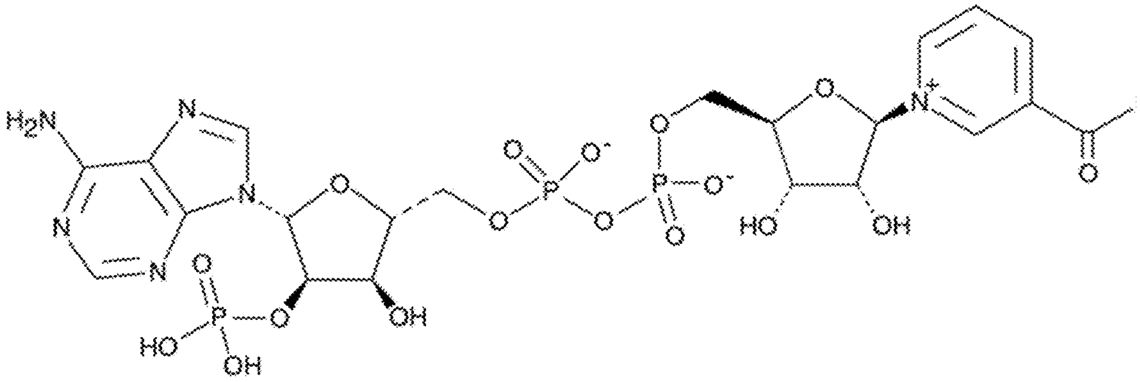
Figure 4E:
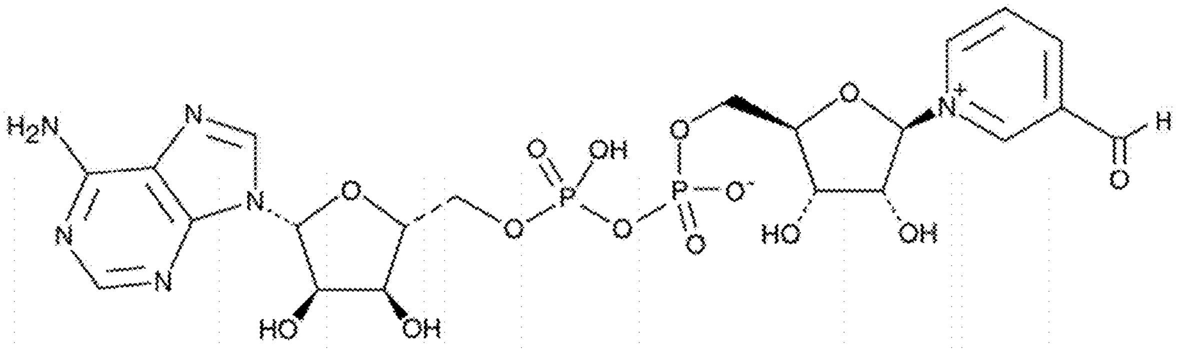
Figure 4F:
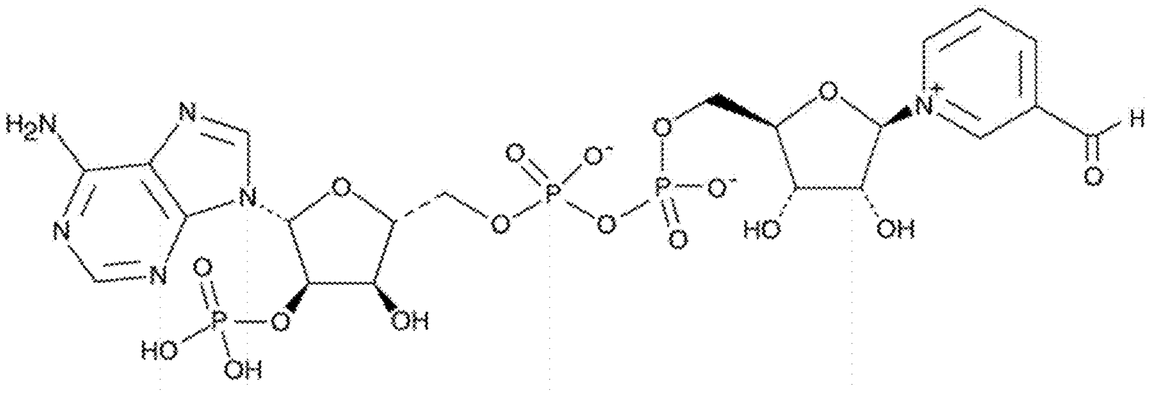
Figure 4G:
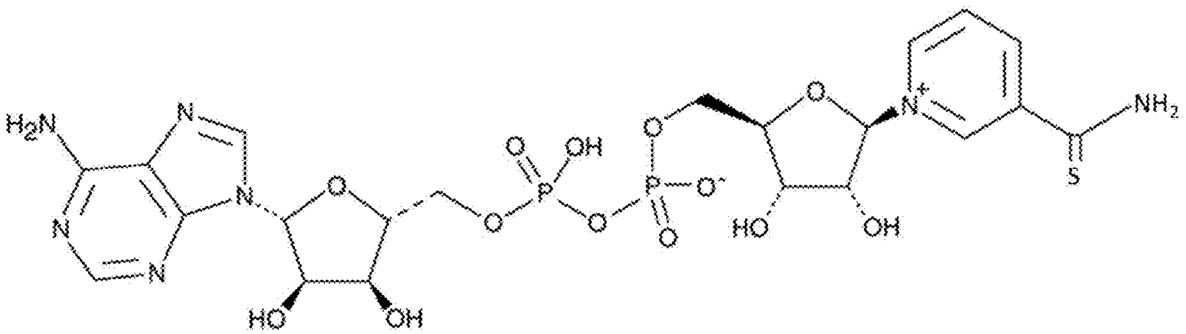
Figure 4H:
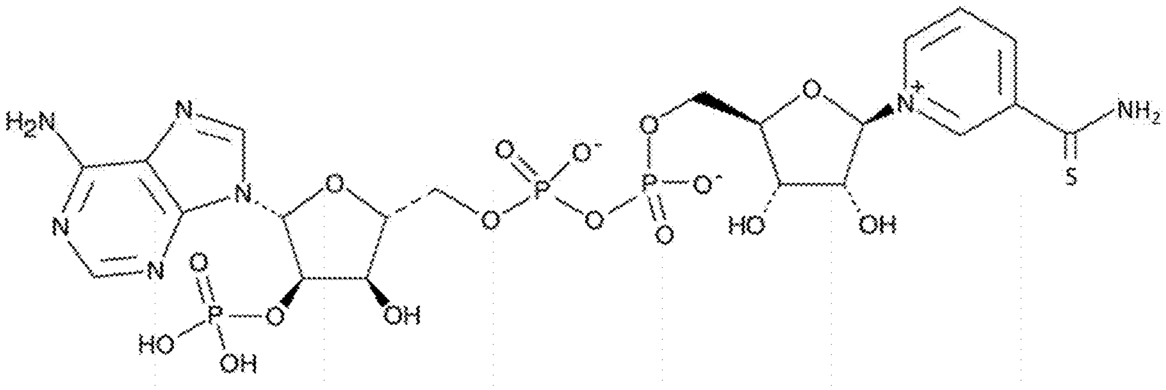

Diagnostic Determination of Ammonia in a Plasma Sample Using an Assay Kit of the Prior Art (Assay Designation "$NH_3$")

A Roche Cobas® $NH_3$ (Ammonia) assay kit for Roche/Hitachi analyzers (including the MODULAR P platforms; assay kit obtained from Roche Diagnostics GmbH, Mannheim, Germany, Cat. No. 11877984216 with Cat. Nos. 20751995190, 20752401190, 20753009190 as calibrators) was provided.

Prior to use, R2 was prepared in three steps, thereby bringing in solution a solid (i.e. water-free) preparation of NADPH:

(1) Providing each of one bottle 2a and one bottle 2b which are supplied as parts of the assay kit, followed by reconstituting the contents of bottle 2b by adding 0.5 mL of reagent from bottle 2a into bottle 2b and mixing, followed by incubating the mixture for 10 minutes at room temperature, with occasional gentle swirling, thereby obtaining a first solution in bottle 2b.

(2) Providing one bottle 2 supplied as part of the assay kit and the bottle 2a from step (1), followed by reconstituting the contents of bottle 2 by adding 4.5 mL of reagent from bottle 2a into bottle 2, and mixing by gentle inversion, thereby obtaining a second solution in bottle 2.

(3) Providing the bottle 2b with the first solution obtained as a result of step (1), and providing the bottle 2 with the second solution obtained as a result of step (2), adding 150 µl of the first solution from bottle 2b to the second solution in bottle 2, and mixing by gentle inversion, thereby obtaining ready-to-use R2 working solution.

The working solution R1 provided as part of the kit contained triethanolamine buffer: 151 mmol/L, pH 8.6; 2-oxoglutarate: 16.6 mmol/L; ADP: ≥1.2 mmol/L; and additionally preservatives.

The ready-to-use working solution R2 obtained as a result of step (3) detailed above contained NADPH: ≥458 µmol/L; GLDH (bovine liver; 25° C.): ≥24.3 U/mL; triethanolamine buffer: 151 mmol/L, pH 8.6; 2-oxoglutarate: 16.6 mmol/L; ADP: ≥1.2 mmol/L; and additionally preservatives.

The assay kit, specifically R1 and R2 was/were used according to the instructions of the manufacturer on a Roche/Hitachi MODULAR P platform.

EXAMPLE 2

Scavenging of Ammonia by Way of Adding Different Amounts of GLDH into R2

R2 working solution was prepared as described in Example 1. Aliquots were mixed with different amounts of GLDH

EXAMPLE 3

Diagnostic Determination of Ammonia in a Plasma Sample Using the Novel Assay Kit with Enhanced Stabilization of NADPH (Assay Designation "$NH_3L2$")

A newly developed Cobas® $NH_3L2$ (Ammonia) assay kit for Roche/Hitachi analyzers (including the cobas c platforms c 311, c 501/502; assay kit composed by the inventors, using Cat. Nos. 20751995190, 20752401190, 20753009190 as calibrators) was provided. The kit comprises two different working solutions, R1 and R3 which are ready-to-use.

The working solution R1 provided as part of the kit contained BICINE (=N,N-bis(2-hydroxyethyl)-glycine) buffer: 300 mmol/L, pH 8.3; GLDH (microbial): ≥16.7 µkat/L; detergents; preservative.

The working solution R3 provided as part of the kit contained GLDH (microbial): ≥5.0 µkat/L; 2-oxoglutarate: 78 mmol/L; NADPH: ≥1.3 mmol/L; stabilizer; nonreactive buffer.

The assay kit, specifically R1 and R3 was/were used according to instructions as depicted in FIGS. 3A-C on a Roche/Hitachi cobas c platform.

EXAMPLE 4

Scavenging of Ammonia by Way of Adding Different Amounts of GLDH into R2

TABLE 1

| # | Amount of GLDH added to solution, in U/mL | $NH_3$-spiked | Incubation time | Incubation temperature |
|---|---|---|---|---|
| 1 | None (=0) | No | n.a. | 2° C. to 8° C. |
| 2 | None (=0) | Yes | n.a. | 2° C. to 8° C. |
| 3 | None (=0) | No | 7 d | 35° C. |
| 4 | None (=0) | No | 10 d | 35° C. |
| 5 | None (=0) | No | 14 d | 35° C. |
| 6 | 1 | No | n.a. | 2° C. to 8° C. |
| 7 | 1 | Yes | n.a. | 2° C. to 8° C. |
| 8 | 1 | No | 7 d | 35° C. |
| 9 | 1 | No | 10 d | 35° C. |
| 10 | 1 | No | 14 d | 35° C. |
| 11 | 2 | No | n.a. | 2° C. to 8° C. |
| 12 | 2 | Yes | n.a. | 2° C. to 8° C. |
| 13 | 2 | No | 7 d | 35° C. |
| 14 | 2 | No | 10 d | 35° C. |
| 15 | 2 | No | 14 d | 35° C. |
| 16 | 5 | No | n.a. | 2° C. to 8° C. |
| 17 | 5 | Yes | n.a. | 2° C. to 8° C. |
| 18 | 5 | No | 7 d | 35° C. |
| 19 | 5 | No | 10 d | 35° C. |
| 20 | 5 | No | 14 d | 35° C. |
| 21 | 10 | No | n.a. | 2° C. to 8° C. |
| 22 | 10 | Yes | n.a. | 2° C. to 8° C. |
| 23 | 10 | No | 7 d | 35° C. |
| 24 | 10 | No | 10 d | 35° C. |
| 25 | 10 | No | 14 d | 35° C. |
| 26 | 14 | No | n.a. | 2° C. to 8° C. |
| 27 | 14 | Yes | n.a. | 2° C. to 8° C. |
| 28 | 14 | No | 7 d | 35° C. |
| 29 | 14 | No | 10 d | 35° C. |
| 30 | 14 | No | 14 d | 35° C. |

An aqueous solution was freshly prepared, the solution contained 2-oxoglutarate: 78 mmol/L; NADPH: ≥1.3 mmol/L; and nonreactive buffer. Different amounts of GLDH were added to aliquots of the aqueous solution. One aliquot was additionally spiked with a known amount of ammonia. Different incubation conditions were applied to the individually prepared test solutions.

Figure 5:
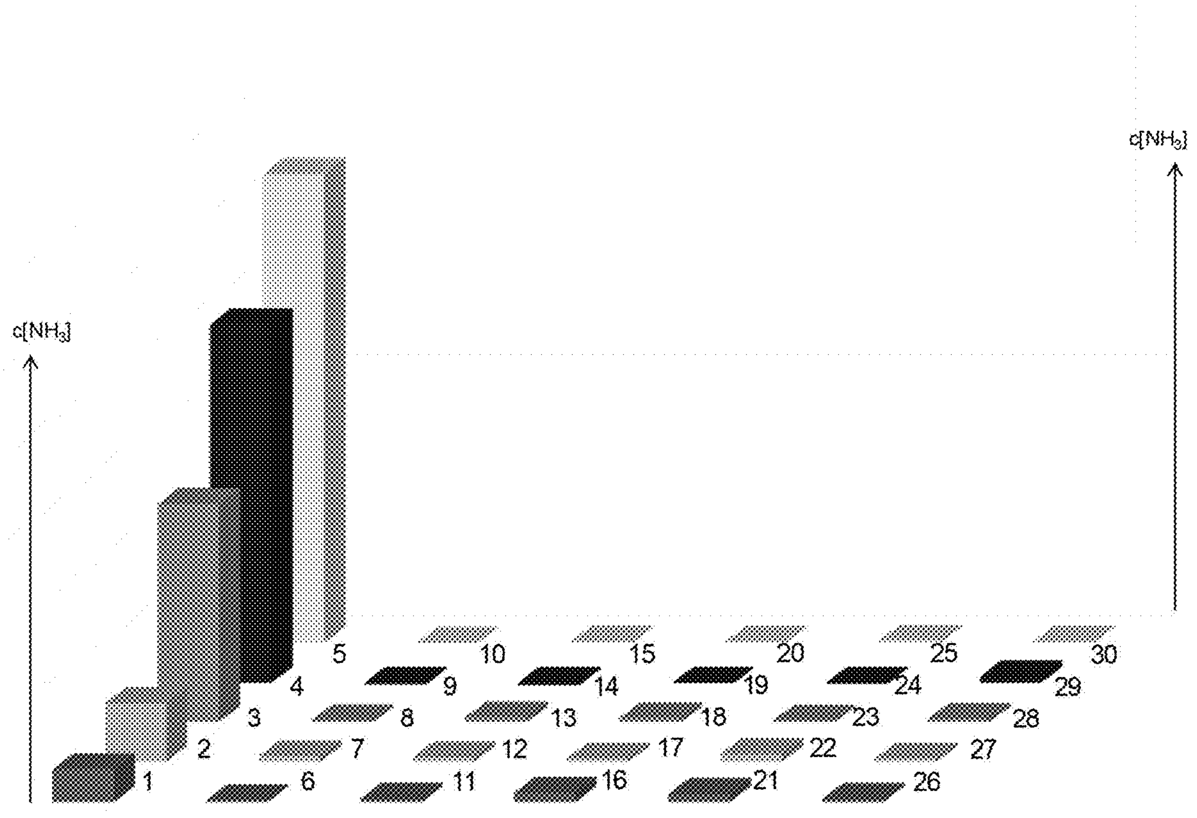
FIG. 5 Graphic representation of the results of the experiments listed in Table 1 (see Example 4 and Table 1).

Table 1 summarizes compositions and conditions. FIG. 5 is a graphical representation of the results, i.e. the ammonia concentration (also referred to as "c[$NH_3$]") detected after each experiment is depicted by the height of each individual block in the 3D diagram. The more a depicted block is extended along the Y-axis given by the arrow in FIG. 5 (i.e. the taller the respective block in the diagram is), the higher the ammonia concentration that was detected in the respective experiment. Each block represents an experiment as given in the numbered list of Table 1, and the number designations given to the single blocks in FIG. 5 correspond to the numbering [#] in Table 1.

Remarkably by means of the presence of GLDH the concentration of ammonia could be kept reproducibly in a range of between 0.01 µM and 1.5 µM. The GLDH-related blocks in the diagram of FIG. 5 correspond to values from 0.02 µM to 1.3 µM.

At the end of the 35° C. incubation of experiments ##10, 15, 20, 25 and 30 (i.e. at the end of the 14 d interval) the surviving GLDH activity remaining in the aqueous solution was determined. Table 2 summarizes the results.

TABLE 2

| # | Initial GLDH activity, in in U/mL | surviving GLDH activity in U/mL after 14 d at 35° C. |
|---|---|---|
| 10 | 1 | 0.13 |
| 15 | 2 | 0.91 |
| 20 | 5 | 1.66 |
| 25 | 10 | 3.53 |
| 30 | 14 | 5.18 |

It should be noted that the incubation conditions applied were designed to mimic the strain provided by a longer time at ambient conditions (e.g. room temperature) on the reagent, and in particular on the enzymatic activity comprised therein. Thus, the implication on reagent shelf life caused by the presence of a GLDH-based scavenging mechanism for ammonia becomes apparent by the data reported here.

It is interesting to see that even the lowest amount of GLDH (experiment #10) was successful in removing any ammonia that was formed during the incubation period. When this is compared to the result of the same solution but in the absence of GLDH (experiment #5) it becomes apparent that even under constraint, i.e. under conditions which are non-optimal for GLDH activity and/or stability, it is well possible to find conditions under which the enzyme is active enough to ensure efficient removal of ammonia from decomposition of the co-substrate.

As the co-substrate is present at a saturating concentration, consumption in the scavenging process was found to be insignificant, i.e. irrelevant for the performance of the newly developed Cobas® $NH_3L2$ (Ammonia) assay kit.

EXAMPLE 5

Stabilized Working Solution with NADH Instead of NADPH

A working solution R3 as given in Example 2 was prepared, and a working solution R3' in which NADH replaced NADPH. Each solution was filled into a cuvette, and the extinction at or near the UV absorption maximum of NADH or NADPH was constantly measured. At one point in time (after 15 min) an ammonia solution was added into the cuvette, adjusting the ammonia concentration in the respective working solution to 100 μM. Extinction was further recorded. It was found that in both working solutions concentration of the co-substrate decreased, as became apparent by decreasing extinction readings. From these data it was concluded that the mechanism of scavenging ammonia from the working solution (by means of GLDH enzymatic activity) worked in the presence of both co-substrates. Measurements were taken at 10° C.

Figure 6:
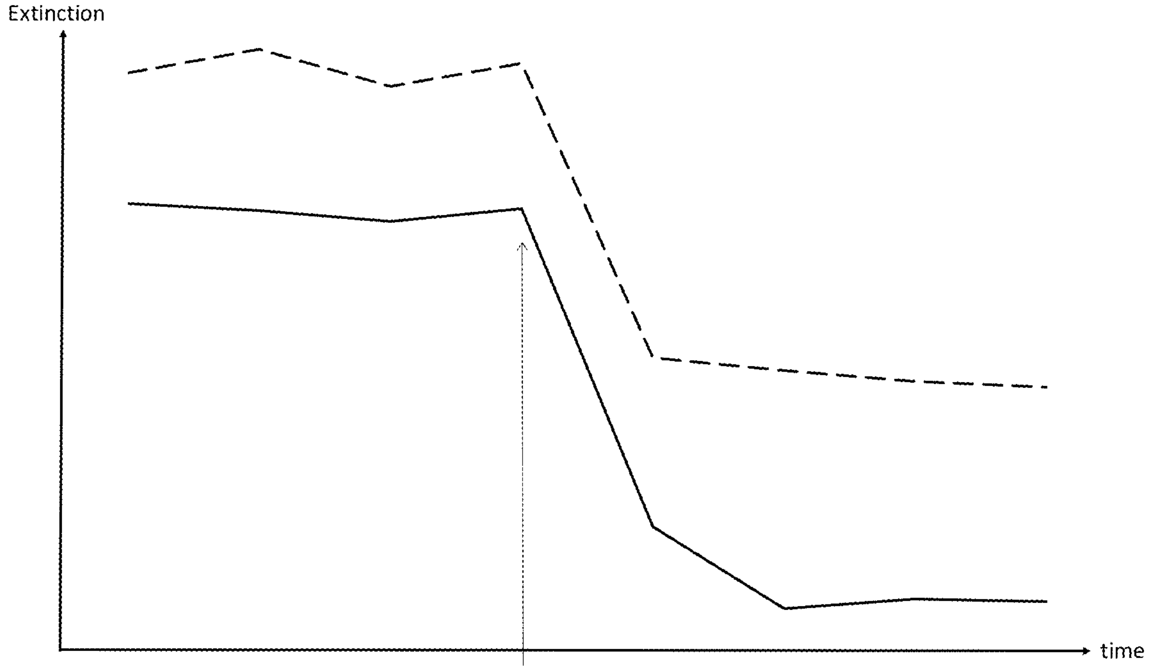
FIG. 6 Comparison of (i) the original second reagent (R3) [solid line] working solution as described in Example 2 (containing NADPH) and (ii) modified working solution R3' (modified second reagent according to the present disclosure) in which NADPH was replaced by NADH [dotted line], for further details see Example 5. Extinction readings for NADPH [solid line] and NADH [dotted line].

FIG. 6 depicts the extinction readings for NADPH (solid line) and NADH (dotted line). The time point of the addition of ammonia is indicated by the thin arrow which also marks the start of co-substrate consumption, indicated by decreasing extinction.

It should be noted here that the amount of ammonia added was very high and was chosen in this concentration to indicate that a low amount of GLDH, even under suboptimal conditions, is capable of reacting ammonium and co-substrate to yield L-glutamate and water, thereby scavenging ammonia from the solution.

The invention claimed is:

1. An assay kit for quantitatively determining the concentration of ammonia in an aqueous liquid sample, the kit containing 2-oxoglutarate, glutamate dehydrogenase (GLDH) capable of reacting nicotinamide adenine dinucleotide phosphate (NADPH) and/or nicotinamide adenine dinucleotide (NADH) as a co-substrate, and NADPH and/or NADH (NAD(P)H), wherein the kit comprises a first and a second container, wherein the first container contains a first aqueous reagent with a first amount of GLDH, the first reagent having a pH capable of maintaining enzymatic activity of GLDH, wherein the second container contains a second aqueous reagent with NAD(P)H, 2-oxoglutarate, and a second amount of GLDH, wherein the GLDH enzymatic activity per mL of the first reagent is higher than the GLDH enzymatic activity per mL reagent in the second reagent, wherein, in the second reagent, ammonia released by decomposition of NAD(P)His removed from the aqueous solution through GLDH enzymatic activity acting upon ammonia, NAD(P)H and 2-oxoglutarate thereby forming L-glutamate, NAD(P)+ and $H_2O$, wherein the pH of the second reagent is capable of maintaining enzymatic activity of GLDH in the second reagent, and wherein the concentration of ammonia in the second reagent is from about 0.01 μM to about 1.5 μM.

2. The assay kit of claim 1, wherein NAD(P)H is present only in the second reagent.

3. The assay kit of claim 1, wherein the pH of the first reagent is from pH 7 to pH 9.

4. The assay kit of claim 1, wherein the pH of the second reagent is from pH 8 to pH 11.

5. The assay kit of claim 1, wherein the ratio between the GLDH enzymatic activity per mL of the first reagent and the GLDH enzymatic activity per mL of the second reagent is from 1.5:1 to 15:1.

6. The assay kit of claim 1, wherein relative to the total GLDH enzymatic activity provided by the reagents comprised in the kit the second reagent contains an amount of GLDH enzymatic activity from 1% to 30%.

7. The assay kit of claim 1, wherein the first reagent contains a buffer selected from N,N-bis(2-hydroxyethyl)-glycine and triethanolamine.

8. The assay kit of claim 1, wherein the first reagent contains a detergent.

9. The assay kit of claim 1, wherein the second reagent is obtained by the steps of (a) dissolving in an aqueous solution 2-oxoglutarate, GLDH, and NAD(P)H, and adjusting the pH of the second reagent to be permissive for maintaining enzymatic activity of GLDH in the second reagent to convert ammonia, NAD(P)H, and 2-oxoglutarate, followed by (b) incubating the aqueous solution obtained from step (a) at 35° C. for 14 d, wherein the concentration of ammonia in the second reagent is from about 0.02 μM to about 1.3 μM.

10. A method to provide an assay kit for quantitatively determining the concentration of ammonia in an aqueous liquid sample, the kit comprising two different aqueous reagents, the reagents containing in aqueous solution 2-oxoglutarate, glutamate dehydrogenase (GLDH) capable of reacting nicotinamide adenine dinucleotide phosphate (NADPH) and/or nicotinamide adenine dinucleotide (NADH) as a co-substrate, and NADPH and/or NADH (NAD(P)H), the method comprising the steps of preparing a first reagent by dissolving GLDH in an aqueous solution with a pH capable of maintaining enzymatic activity of GLDH, preparing a second reagent by dissolving in an aqueous solution 2-oxoglutarate, GLDH, and NAD(P)H, and adjusting the pH of the second reagent to maintain enzymatic activity of GLDH in the second reagent to remove ammonia released by decomposition of NAD (P)H from the aqueous solution through GLDH enzymatic activity acting upon ammonia, NAD(P)H, and 2-oxoglutarate, thereby forming L-glutamate, NAD(P)$^+$ and $H_2O$ in the second reagent, providing the first and the second reagent in separate containers, and combining the containers in a kit of parts, thereby providing an assay kit for quantitatively determining the concentration of ammonia in an aqueous liquid sample, wherein the concentration of ammonia in the second reagent is from about 0.01 μM to about 1.5 μM.

* * * * *